US009640168B2

(12) United States Patent
Nooralahiyan et al.

(10) Patent No.: US 9,640,168 B2
(45) Date of Patent: May 2, 2017

(54) NOISE CANCELLATION WITH DYNAMIC RANGE COMPRESSION

(71) Applicant: ElaraTek Ltd., Leeds (GB)

(72) Inventors: Amir Nooralahiyan, Leeds (GB); Bahador Pakbaz, Tehran (IR)

(73) Assignee: ElaraTek LTD., Leeds (GB)

( * ) Notice: Subject to any disclaimer, the term of this patent is extended or adjusted under 35 U.S.C. 154(b) by 0 days.

(21) Appl. No.: 14/726,777

(22) Filed: Jun. 1, 2015

(65) Prior Publication Data

US 2016/0005389 A1 Jan. 7, 2016

(30) Foreign Application Priority Data

Jun. 13, 2014 (GB) .................................. 1410598.5

(51) Int. Cl.

*A61F 11/06* (2006.01)
*G10K 11/16* (2006.01)
*H03B 29/00* (2006.01)
*G10K 11/178* (2006.01)

(52) U.S. Cl.

CPC .. *G10K 11/1782* (2013.01); *G10K 2210/1081* (2013.01); *G10K 2210/3016* (2013.01); *G10K 2210/3056* (2013.01)

(58) Field of Classification Search

CPC ............... G10K 11/16; G10K 11/1784; G10K 2210/1053; G10K 2210/1081; H04R 25/00; H04R 3/005; H04R 2410/05

USPC ............. 381/71.11, 74, 23.1, 57, 71.14, 94.1

See application file for complete search history.

(56) References Cited

U.S. PATENT DOCUMENTS 9,031,271 B2 * 5/2015 Pontoppidan ........ H04R 25/353 381/23.1
9,319,019 B2 * 4/2016 Selig ...................... H03G 5/165
2016/0020744 A1 * 1/2016 Kok ......................... H03G 3/32 381/57

FOREIGN PATENT DOCUMENTS

WO 2011041738 4/2011

* cited by examiner

*Primary Examiner* — Thjuan K Addy

(74) *Attorney, Agent, or Firm* — Patti & Malvone Law Group, LLC

(57) ABSTRACT

An audio processor (200) for a hearing device has a noise estimator (100), an adaptive noise canceller (110), and a dynamic range compressor (120) to provide a gain according to a signal strength of an input signal. A signal strength processor (130) determines a signal strength dependent noise cancellation parameter, and the adaptive noise canceller provides noise cancellation of the input signal according to an estimated noise from the noise estimator, and according to the signal strength dependent noise cancellation parameter, so as to provide less noise cancellation when the input signal has higher signal strength than when the input signal has a lower signal strength. This helps retain the desirable environment or ambient type noise, present when the signal strength is higher, while providing more cancellation of undesirable circuit type noise when there is low input signal strength.

20 Claims, 11 Drawing Sheets

NOISE CANCELLATION WITH DYNAMIC RANGE COMPRESSION

TECHNICAL FIELD

The present invention relates to audio processors such as signal processors, to integrated circuits having such signal processors, to hearing devices, to methods of processing an input signal, and to computer programs for such methods.

BACKGROUND

Noise is a significant concern in many communication systems and devices, including mobile phones; personal radios; wired or wireless headsets; in-the-ear (ITE) headsets; hearing protectors; and hearing aid devices. There are many sources of noise, including different types of environmental sounds and ambient noises; as well as noises generated within the hardware circuitries, particularly digital hardware circuits utilising CODECs, (Coder Decoder) ADCs (Analog to Digital Converter), DACs (Digital to Analog Converter), and DSPs (Digital Signal Processors) for audio signal processing and speech enhancement. In all these cases, the noise is accumulated at various stages of the communication system and is added to the original speech. The received final signal to the end-user therefore consists of the combined original speech and all different noise increments added during transmission.

In the case of noise generated in the hardware devices such as CODECs and/or DSPs, the circuit noise is present regardless of any external or ambient sounds or noises. This type of noise becomes very prominent when there's no ambient sound present, such as in a quiet room. The circuit noise level is directly proportional to the gain (amplification) applied in the device. Such amplification exacerbates the discomfort and annoyance to the user and can cause significant listening strain and fatigue. It can also adversely affect the quality of incoming speech. Typical examples of devices suffering from such inherent hardware noises are: call centre headsets using a digital amplifier, digital In-The-Ear (ITE) headsets/protectors and digital Hearing-Aid/Hearing-Assist devices.

As acknowledged in U.S. Pat. No. 8,126,176, in a conventional hearing aid, inputted sound is amplified without making any distinction between speech and sounds other than speech. The amplified sound is outputted to the person wearing the hearing aid. Accordingly, when environmental noise other than speech becomes loud, this may become uncomfortable for the person wearing the hearing aid. A technique has been proposed in which noise is suppressed by spectrum subtraction (SS), and the amplification ratio is varied according to the ratio between the signal power in a non-speech segment and the signal power of the inputted sound. Spectrum subtraction is a noise suppression processing method in which just the noise component is subtracted from a digital input signal by statistical estimation of the noise level of a non-speech segment.

In U.S. Pat. No. 8,126,176, a hearing aid is shown in which noise suppression processing and nonlinear compression processing are combined so that speech can be clearly heard. The hearing aid has a microphone for producing an input signal from input sound, a noise suppressor for estimating the noise component strength included in the input signal on the basis of the signal strength for each of a plurality of frequency bands in the input signal. For each of the plurality of frequency bands a noise suppression gain for suppressing the noise component strength is calculated, an adjustment amount is calculated on the basis of the signal strength and the noise component strength. The adjustment amount from the noise suppression part is used by the nonlinear compressor for calculating a reference gain on the basis of the signal strength and the specific reference gain, and adjusting the reference gain on the basis of the adjustment amount. Thus for each of the plurality of frequency bands a nonlinear compression gain for nonlinearly compressing and amplifying the input signal is calculated. A receiver reproduces an output sound from the output signal.

SUMMARY

Embodiments of the invention can provide improved apparatus or methods or computer programs. According to a first aspect of the invention, there is provided an audio processor suitable for processing an input signal and having a noise estimator, an adaptive noise canceller, a dynamic range compressor configured to provide a gain for the input signal adapted according to a signal strength of the input signal and a signal strength processor for determining a signal strength dependent noise cancellation parameter, based on an indication of signal strength. The adaptive noise canceller is configured to provide noise cancellation of the input signal according to an estimated noise from the noise estimator, and according to the signal strength dependent noise cancellation parameter, so as to provide less noise cancellation when the input signal has higher signal strength than when the input signal has lower signal strength.

A benefit of providing reduced cancellation when there is higher signal strength is that more of the desirable ambient type noise, present when the signal strength is higher, can be retained, while providing more cancellation of undesirable circuit type noise when there is low signal strength. Such circuit type noise can be particularly noticeable to a human ear when there is low signal strength, and can be amplified by the operation of the dynamic range compressor which may incorporate an expander (amplifier) region for the low input signals.

Any additional features can be added to any of the aspects, or disclaimed, and some of such additional features are described and some set out in dependent claims. One such additional feature is the signal strength processor having a selector configured to select a maximum amount of noise cancellation by the adaptive noise canceller, according to the signal strength and the signal strength dependent noise cancellation parameter comprising an indication of this selection. This is one way of providing control of the noise cancellation. It effectively causes a scaling of the amount of noise cancellation so that some noise is retained in most cases. This can provide some comfort or reassurance to a listener that the input signal is still present, and thus make the noise cancellation seem less obtrusive and more natural.

Another such additional feature is the adaptive noise canceller being configured to provide variation in the noise cancellation according to variation in the signal strength dependent noise cancellation parameter, with a granularity sufficiently fine so that a listener does not perceive step changes in a noise level, This can help provide a perception in a listener that a level or proportion of noise is remaining constant even as the signal level changes dynamically, and as the dynamic range compressor alters the gain. This perceived constant noise can help reduce or avoid irritation or fatigue in a listener, caused by unnatural sounding changes in perceived noise level. Another such additional feature is the signal strength processor having a signal strength estimator configured to determine a signal strength of the input signal and an adjuster to generate a gain adjusted signal strength indication according to a characteristic of gain versus signal strength used by the dynamic range compressor, and to determine the signal strength dependent noise cancellation parameter according to the gain adjusted signal strength indication. This adjustment can enable better control of the noise cancellation that is based on a signal strength value that is closer to what a user would hear. Also it can provide better results during highly dynamic signals, since it will tend to reduce the magnitude of rapid changes in the amount of noise cancellation.

Another such additional feature is the signal strength processor being coupled to determine the signal strength dependent noise cancellation parameter according to the input signal before the adaptive noise cancellation. This is one of several possible sources for the calculation of this parameter, and will tend to lead to more accurate results than other sources because the input signal is more raw.

Another such additional feature is the signal strength processor being coupled to determine the signal strength dependent noise cancellation parameter according to the input signal after the adaptive noise cancellation. This is another of several possible sources for the calculation of this parameter, and will tend to lead to less accurate results because the input signal may have lost some information, but there may be a saving in processing resource.

Another such additional feature is a change detector for detecting an increase or decrease in the signal strength of the input signal, and the dynamic range compressor having a smoother configured to smooth changes in the gain according to the detected change. This can enable the gain to adapt quickly when needed, for example to reduce gain for sharp increases in signal strength, and to adapt less quickly when needed, for example during a decrease, so that dips between peaks are not followed, to reduce noticeable oscillations in amount of noise cancellation.

Another such additional feature is a frequency band analyser for determining powers of the input signal in a plurality of frequency bands, and the adaptive noise canceller comprising canceller components each configured to operate on a respective one of the plurality of frequency bands. This is a particularly useful way of carrying out the noise cancellation. Another aspect of the invention provides an integrated circuit having the audio processor set out above.

Another aspect of the invention provides a hearing device having an audio processor as set out above, and a microphone coupled to provide an input signal to the audio processor, and an audio output device coupled to the audio processor.

Another aspect of the invention provides a method of processing an input signal having steps of providing a gain for the input signal adapted according to a signal strength of the input signal and according to a dynamic range compression characteristic, determining a signal strength dependent noise cancellation parameter, based on the signal strength and providing noise cancellation of the input signal according to an estimated noise, and according to the signal strength dependent noise cancellation parameter, so as to provide less noise cancellation when the input signal has higher signal strength than when the input signal has a lower signal strength.

Another such additional feature is the step of determining the signal strength dependent noise cancellation parameter comprising selecting a maximum amount of noise cancellation by the adaptive noise canceller according to the signal strength.

Another such additional feature is the step of determining the signal strength dependent noise cancellation parameter having steps of determining a signal strength of the input signal, generating a gain adjusted signal strength indication according to the dynamic range compression characteristic, and determining the signal strength dependent noise cancellation parameter according to the gain adjusted signal strength indication.

Another such additional feature is the step of determining the signal strength dependent noise cancellation parameter being made using the input signal before the noise cancellation is applied.

Another such additional feature is having the step of detecting a sign of a change in the signal strength of the input signal, and the step of providing a gain being configured to provide a gain smoothed according to the detected sign of the change.

Another aspect of the invention is a computer program on a computer readable storage medium, and having instructions which when executed by a processor, cause the processor to carry out the steps of the method.

Numerous other variations and modifications can be made without departing from the claims of the present invention. Therefore, it should be clearly understood that the form of the present invention is illustrative only and is not intended to limit the scope of the present invention.

BRIEF DESCRIPTION OF THE DRAWINGS

How the present invention may be put into effect will now be described by way of example with reference to the appended drawings, in which.

DETAILED DESCRIPTION

Figure 1:
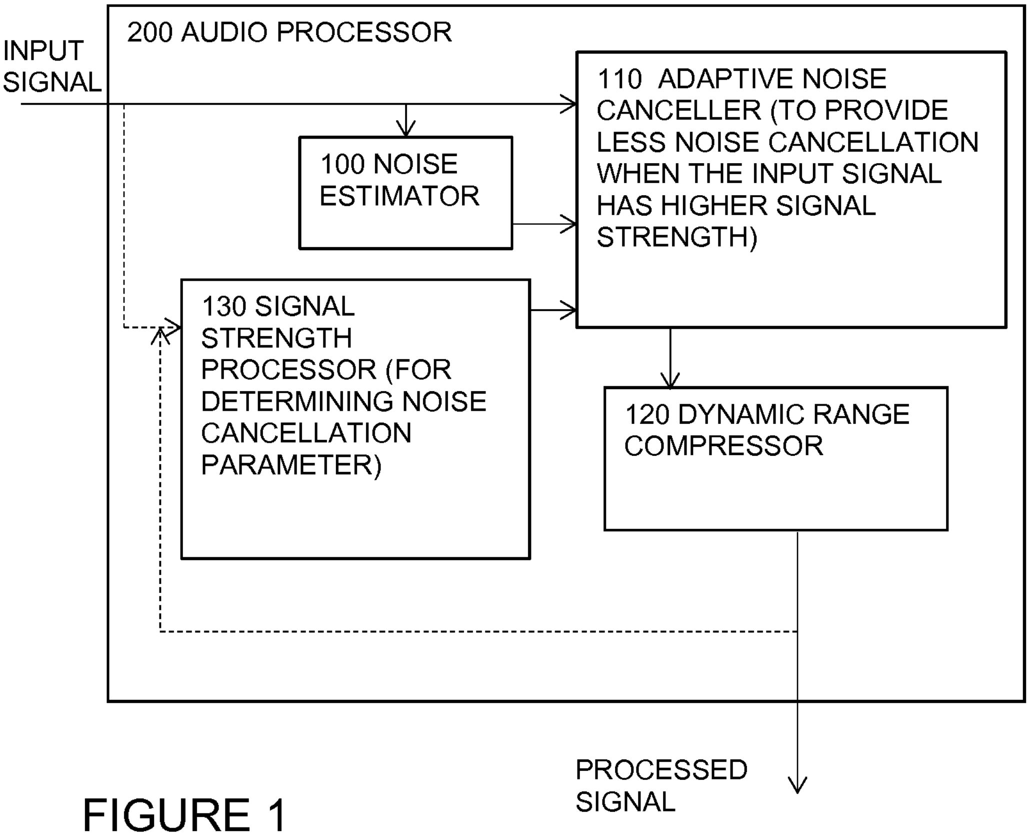
FIG. 1 shows a schematic view of an audio processor according to an embodiment.

The present invention will be described with respect to particular embodiments and with reference to drawings but note that the invention is not limited to features described, but only by the claims. The drawings described are only schematic and are non-limiting. In the drawings, the size of some of the elements may be exaggerated and not drawn to scale for illustrative purposes.

Definitions:

Where the term "comprising" is used in the present description and claims, it does not exclude other elements or steps and should not be interpreted as being restricted to the means listed thereafter. Where an indefinite or definite article is used when referring to a singular noun e.g. "a" or "an", "the", this includes a plural of that noun unless something else is specifically stated.

References to programs or software can encompass any type of programs in any language executable directly or indirectly on any computer.

References to computer or processor are intended to encompass any kind of processing hardware which can be implemented in any kind of logic or analog circuitry, integrated to any degree, and not limited to general purpose processors, digital signal processors, ASICs, FPGAs, discrete components or logic and so on, and are intended to encompass implementations using multiple processors which may be integrated together, or co-located or distributed at different locations for example.

References to less in the context of less noise cancellation when the input signal has a higher signal strength are intended to encompass less relative to a reference, such as when there is a lower signal strength, so the absolute amount of noise cancellation at higher signal strength can be constant or vary either way, while still providing less noise cancellation relative to the noise cancellation at some lower signal strength.

Introduction to Embodiments

By way of introduction, some issues with current Adaptive Noise Cancellers will be discussed. Software noise cancellation can often be used to remove inherent hardware noises; however such noise cancellation techniques do not discriminate between the hardware generated noise and other external sources of noise. In many applications removing external noise is not desirable, therefore the challenge is to remove the inherent hardware noise without actually removing any ambient noise which may include important information content. A typical example of such requirement is in hearing aid; hearing assist or hearing protector device whereby there may be a significant inherent hardware circuit noise, especially when additional gain (signal amplification) is applied. At the same time ambient noises, for example traffic noise, must remain intact as they provide important environment information to a person wearing a hearing aid device. Other use cases include a hearing protection headset with talk-through microphones for listening to ambient sounds. In many cases the ambient sounds convey important information which must not be removed by the noise canceller, while the inherent hardware noise can be a distraction and may even mask important content of external (ambient) sounds.

In such devices as hearing protection headsets with talk-through (or environment) microphones, there's often a dynamic range compressor to protect the users' hearing in the event of sudden loud sounds in the close proximity of the user. One example of such use is in hunting or shooting whereby the users wear headsets with talk-through microphones to listen to environmental sounds while the dynamic range compressor protects their hearing against sudden loud gunshots. There are a number of other applications such as hearing aid devices or military headsets whereby it is desirable for the environmental sounds (including different noise types) to remain intact while the inherent circuit noise generated by the electronics hardware is removed.

Some of the embodiments as described below can remove this type of undesirable hardware generated noise without removing the potentially important environmental noise sounds. They can be implemented in various forms, one such form is software running on a Digital Signal Processor (DSP) device designed for many headset types and application, though some or all of the modules or parts of them can be implemented in hardware. The main modules can include an Adaptive Noise Canceller (ANC), a Dynamic Range Compressor (DRC), and some way of providing the dependency of the ANC on the signal strength. In some cases, for more accuracy, this dependency can be calculated in relation to the signal strength as modified according to the gain versus signal strength characteristic of the DRC.

Dynamic Range Compressors DRC

Dynamic Range Compressors (DRCs) are available on many devices, offering audio and speech-related enhancements and hearing protection. A typical application of DRC is to compress the loudest parts (peaks) of the signals while boosting the overall gain of the signal. In effect the quiet sounds become louder, while louder sounds remain unchanged. This technique is often used to make music sound louder in public places without increasing the potentially harmful peak amplitudes of the signal. The technique is also used in broadcasting, music reproduction and signal transmission whereby adverse effect of channel with limited dynamic range is avoided or minimised.

Another important application of DRC is in hearing aids whereby ambient audio levels are matched to the listeners' hearing range based on the results of individuals' hearing test. The DRC is also used in hearing protection devices in the form of circumaural headsets (such as aviation or military headsets) or in-the-ear (ITE) headsets, all of which encompass external microphone(s) for listening to ambient sounds or conversing with another person. Such hearing protection devices allow sounds to be heard at normal volume levels while attenuating loud sounds and high energy acoustic incidents. They can also amplify softer lower level sounds for enhanced intelligibility. Such hearing protection devices allow, for example, hunters to converse normally, with the confidence of knowing that sound of high energy acoustic incidents such as a gunshot will be attenuated to maximum specified level of the DRC. Similarly it offers hearing protection to musicians listening to the music with DRC attenuating the loud noises such as drum beats.

One downside with increasing the gain on low level signals is the increased level of inherent hardware noise in the device or the system. Such inherent noises can be annoying and tiring, especially when devices such as hearing aids and In-The-Ear (ITE) headsets and hearing protectors are worn in the ear with a transducer closely coupled to the human eardrum. This problem is particularly acute when there's little or no ambient sound present (such as a quiet environment) with the high audible circuit noise constantly blasting inside the ear-canal. This constant noise can be annoying and can cause unnecessary listening fatigue.

When ambient sound (voice, ambient noise, etc.) is present the inherent circuit noise is less noticeable and maybe masked by the ambient sound. As the level of ambient sound increases, the compression ratio of the DRC suppresses the inherent circuit noise. The increased noise problem is addressed adequately in some digital versions of such devices whereby a digital signal processor analyses the signal and an adaptive noise canceller algorithm removes significant portion of the noise floor present as a result of gain increase. There are however disadvantages of using a noise canceller algorithm that aggressively and constantly tries to remove the noise from the overall signal. Two main disadvantages are listed below:

1) The noise canceller does not distinguish between the inherent circuit noise caused by the hardware and other important ambient noise types such as traffic noise. In this case a person wearing such a device and naturally relying on his/her hearing maybe put at risk by miss-judging the proximity of an incoming vehicle. In other scenarios, aggressive noise cancellation running at all times may suppress or remove some environmental noises that carry important information content. Such noise reductions on input signals are not desirable.
2) Noise reduction algorithms often remove the noise at the expense of speech quality. Following noise reduction the speech may sound slightly muffled and the intelligibility of the speech may be degraded. This problem is particularly true for less sophisticated noise cancellers running on low power DSPs to maximise battery life.

FIG. 1, Audio Processor According to an Embodiment

Figure 7:
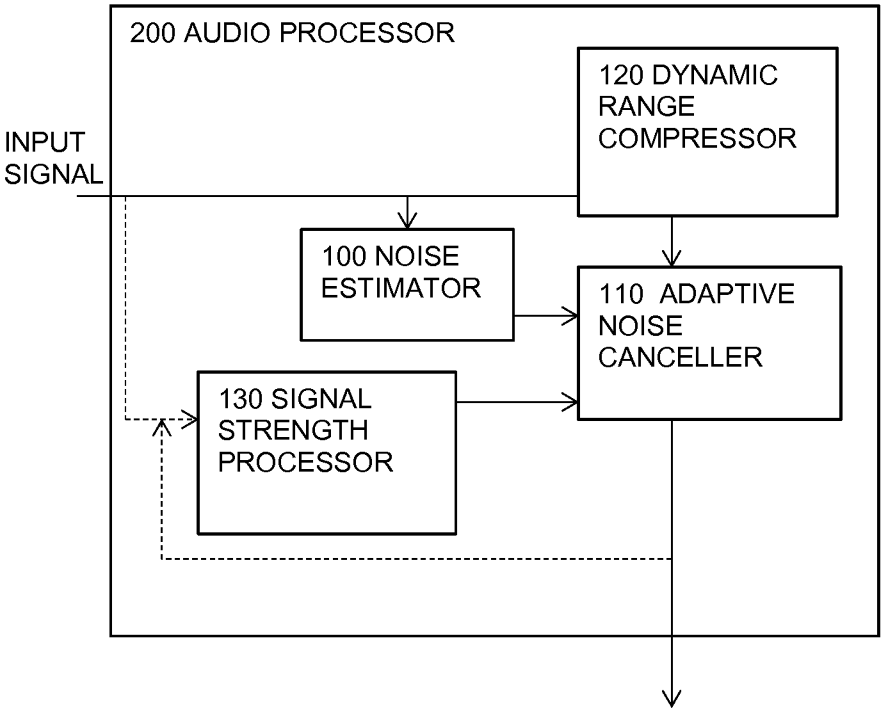
FIG. 7 shows a schematic view of an audio processor according to an embodiment in which the DRC operates ahead of the ANC (Adaptive Noise Canceller)

FIG. 1 shows a schematic view of an audio processor according to an embodiment. An audio processor 200 has an ANC 110, coupled to receive an input signal, and a DRC 120, coupled to receive an output of the ANC. There is a noise estimator 100, to provide an estimate of noise to the ANC. These parts can be implemented in various ways and some examples are described in more detail below. The ANC is arranged to receive a noise cancellation parameter from a signal strength processor 130. The signal strength processor can estimate the signal strength of the input signal, so as to make the parameter signal strength dependent. The ANC is arranged to use this signal strength dependent noise cancellation parameter to provide less noise cancellation when the input signal has higher signal strength compared to when the input signal has lower signal strength. The input signal can be fed to the signal strength processor from any of various points in the audio processor, so alternative paths are shown in dashed lines, either before the input signal is processed by the ANC or at any point after input signal has been processed by the ANC, or after the input signal has been processed by the DRC. Although the DRC is shown coupled after the ANC, in principle an alternative embodiment can provide the DRC coupled before the ANC, to provide a DRC processed input signal to the ANC, as shown in FIG. 7 described below.

Figure 2:
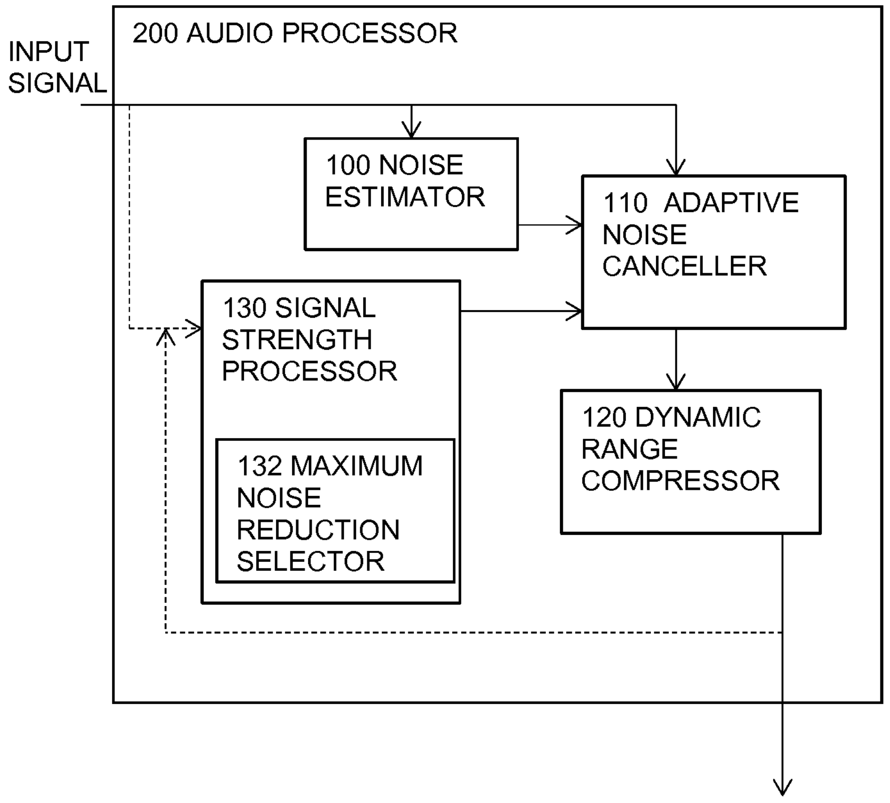
FIG. 2 shows a schematic view of an audio processor according to an embodiment having a selector for selecting a maximum noise reduction.

FIG. 2, Audio Processor Having Selection of Maximum Noise Reduction

FIG. 2 shows a schematic view of an audio processor according to an embodiment having a selector for selecting a maximum noise reduction. This embodiment is similar to that of FIG. 1, and corresponding parts are shown with the same reference numerals. The signal strength processor has a selector for selecting a maximum noise reduction by the ANC, according to the signal strength of the input signal. This is one way of providing the variation of the noise cancellation to enable the benefit that more of the desirable ambient type noise, present when the signal strength is higher, can be retained, while providing more cancellation of undesirable circuit type noise when there is low signal strength. The dependency of noise cancellation on changes in signal strength of the input signal can be continuous or stepwise, and such steps can have a granularity sufficiently fine that a listener does not perceive step changes in noise during dynamic changes in signal strength.

Figure 3:
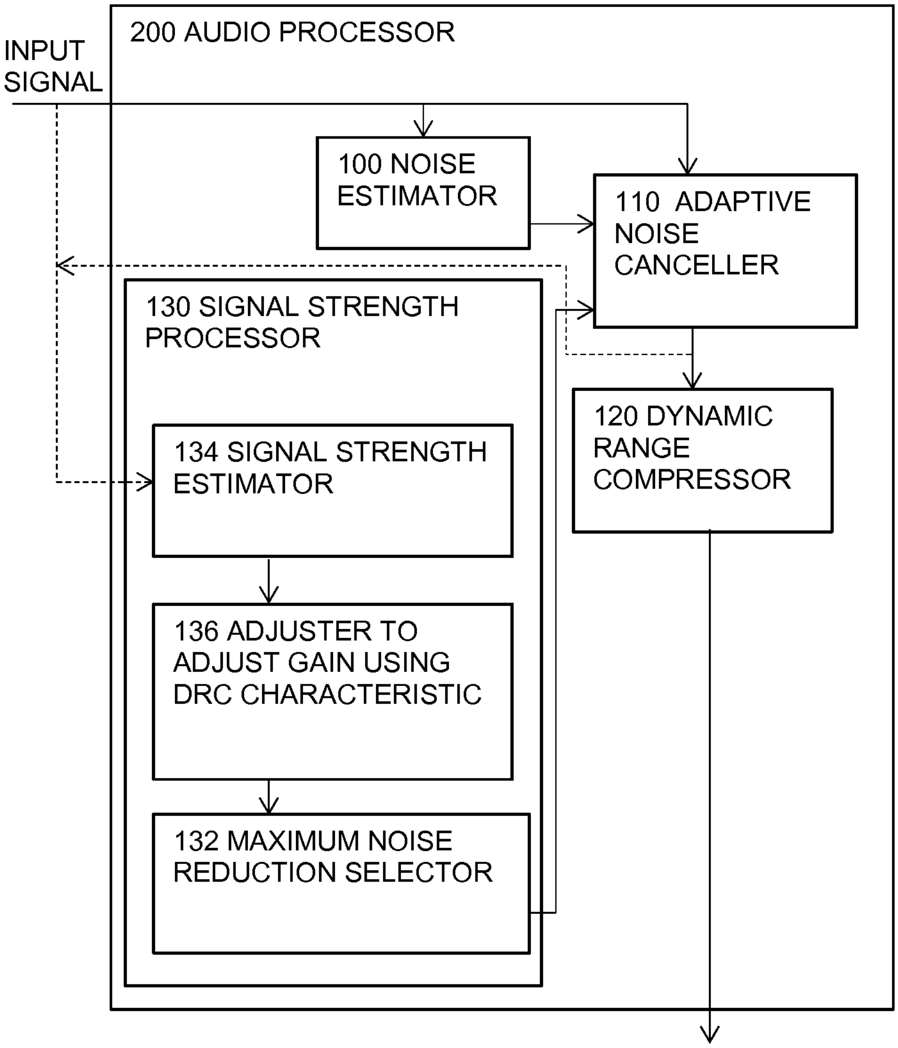
FIG. 3 shows a schematic view of an audio processor according to an embodiment having selection based on signal strength adjusted using a DRC (dynamic range compression) characteristic.

FIG. 3, Parameter Based on Signal Strength Adjusted for DRC

FIG. 3 shows a schematic view of an audio processor according to an embodiment having selection based on signal strength adjusted using a DRC characteristic. This view is similar to that of FIG. 2, and corresponding parts are shown with the same reference numerals. The signal strength processor 130 is shown as having a signal strength estimator 134, an adjuster 136 for adjusting gain using a DRC characteristic, and the maximum noise reduction selector 132. These parts can be implemented in various ways, for example as software modules for execution by a DSP. The ANC and DRC and other parts can also be implemented as software modules for execution by the same DSP. This adjuster can enable better control of the noise cancellation so that it is based on a signal strength value that is closer to what a user would hear. Also it can provide better results during highly dynamic signals, since it will tend to reduce the magnitude of rapid changes in the amount of noise cancellation.

This embodiment shows a Compression-Dependent Adaptive Noise Canceller (CD-ANC) with a noise cancellation parameter that is changed dynamically with respect to the amount of signal strength with compression applied to the instantaneous input signal in real-time. As the compression increases, the amount of noise attenuation by the ANC module can be made to decrease. It can be implemented on an ultra-low-power DSP for battery powered applications such as hearing devices. The inherent circuit noise can be removed when there is little or no input signal (speech and/or ambient noise) present; and yet, as the input signal level increases, a seamless transition to signal compression can be made without any noticeable fluctuation in the level of inherent hardware noise. This is facilitated through accurate estimation of CD-ANC algorithm, constantly adjusting its effective noise cancellation parameter in relation to the amount of compression.

Figure 4:
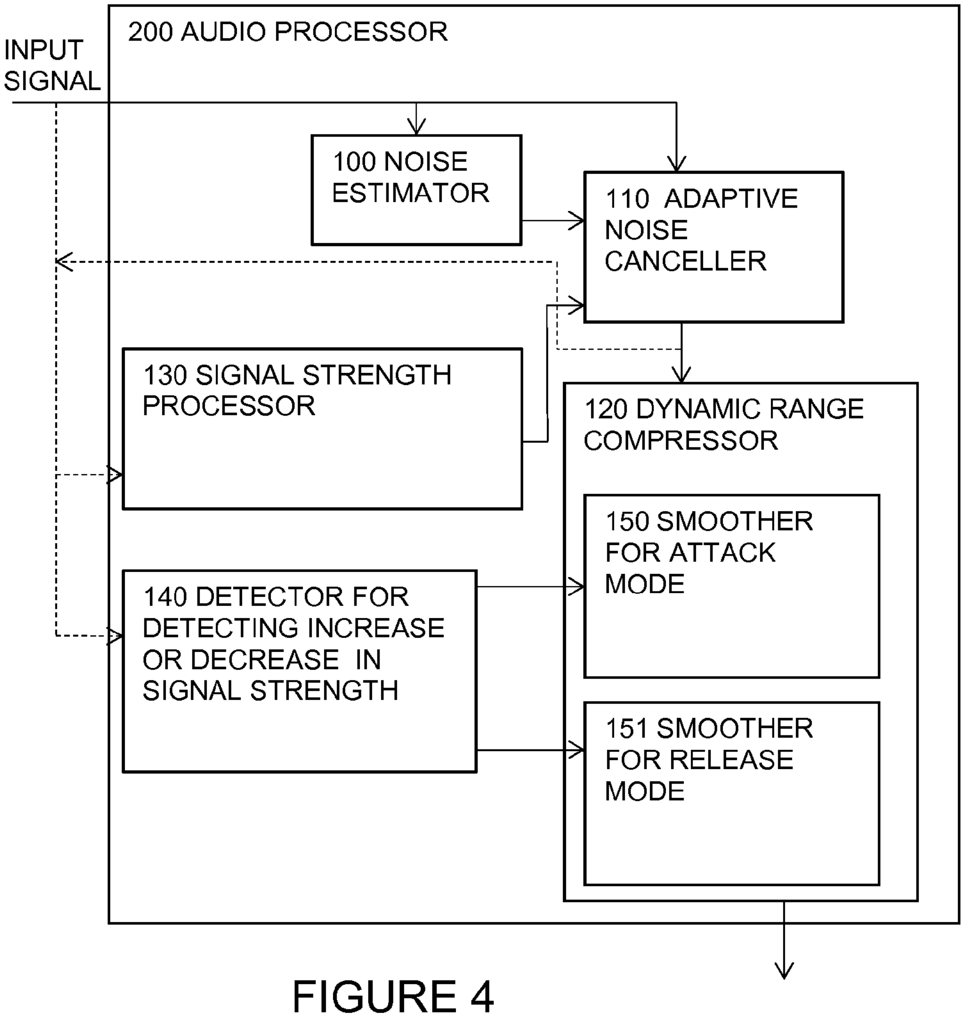
FIG. 4 shows a schematic view of an audio processor according to an embodiment showing smoothing changes in gain in DRC according to detected increase or decrease in signal strength.

FIG. 4, DRC with Smoothing of Changes in Gain

FIG. 4 shows a schematic view of an audio processor according to an embodiment showing smoothing changes in gain in DRC according to detected increase or decrease in signal strength. Again this shows an embodiment similar to that of FIG. 1, and corresponding parts are shown with the same reference signs. In this case there is a change detector 140 for detecting which way (increasing or decreasing) a signal strength of the input signal is changing. Also the DRC has smoothers 150, 151 arranged to smooth the changes in gain applied by the DRC according to a characteristic. The smoothing can be varied to provide different rates of change of gain according to whether the signal strength is increasing (attack) or whether it is decreasing (release). The DRC can therefore provide different attack and release times or rates, to enable the gain to adapt quickly when needed, for example to reduce gain for sharp increases in signal strength, and to adapt less quickly when needed, for example during a decrease. Release time is often longer to avoid noticeable oscillations in the amount of compression during speech gaps.

Figure 5:
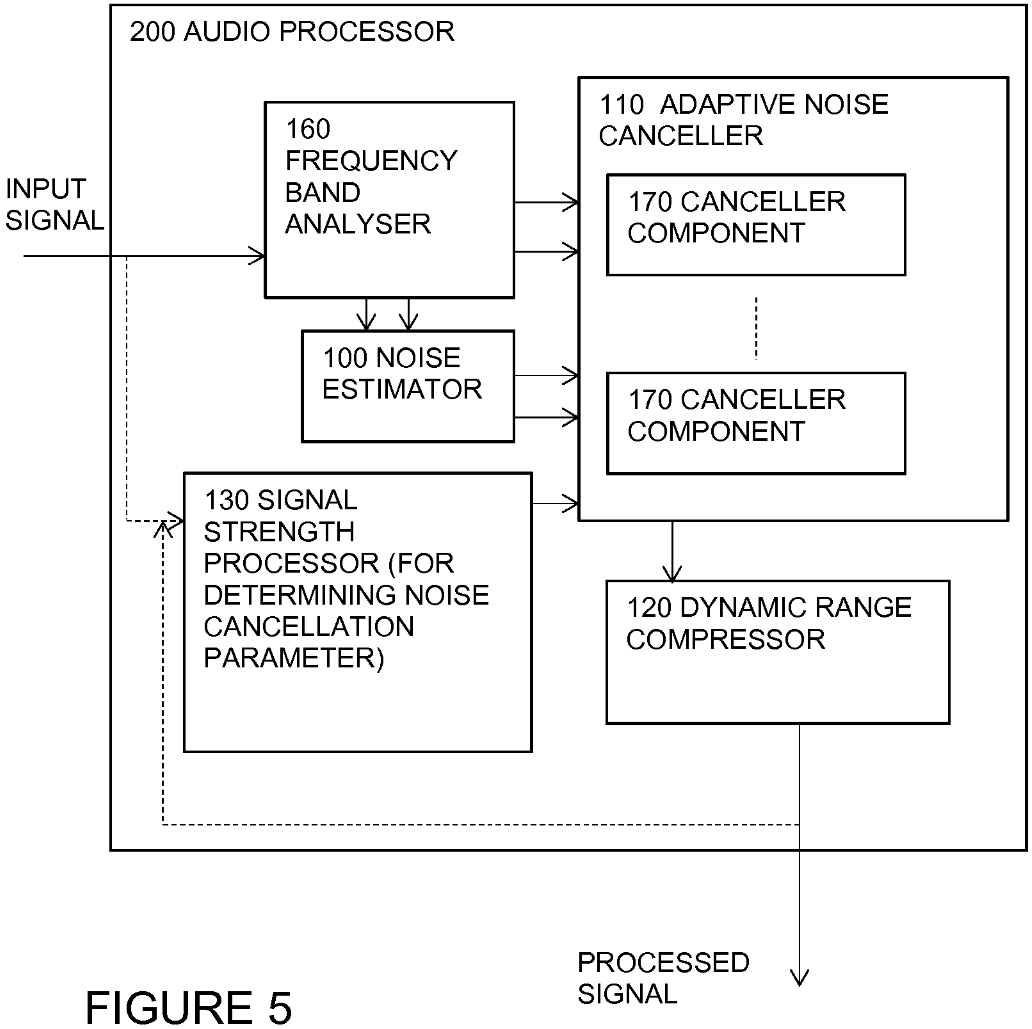
FIG. 5 shows a schematic view of an audio processor according to an embodiment having noise cancellation in frequency bands.

FIG. 5, Noise Cancellation in Frequency Bands

FIG. 5 shows a schematic view of an audio processor according to an embodiment having noise cancellation in frequency bands. Again this shows an embodiment similar to that of FIG. 1, and corresponding parts are shown with the same reference signs. In this embodiment, there is a frequency band analyser 160 for providing an indication of energies in different frequency bands to the ANC and to the noise estimator. The ANC has component cancellers 170 for cancelling noise on each of the frequency bands, depending on the amount of noise detected in each of the frequency bands, by reducing the gain on particular bands for example. This is one way of implementing the ANC and each of the component cancellers can be arranged to have a variable limit on the maximum reduction in gain. These variable limits can be varied according to the noise cancellation parameter fed by the signal strength processor, so as to make the noise cancellation dependent on the signal strength. The noise cancellation parameter is not frequency dependent, so is a single value for all the frequency bands, though in principle embodiments can be envisaged in which there is at least some frequency dependence, with the noise cancellation parameter having multiple values, each for a group of the frequency sub-bands.

Figure 6:
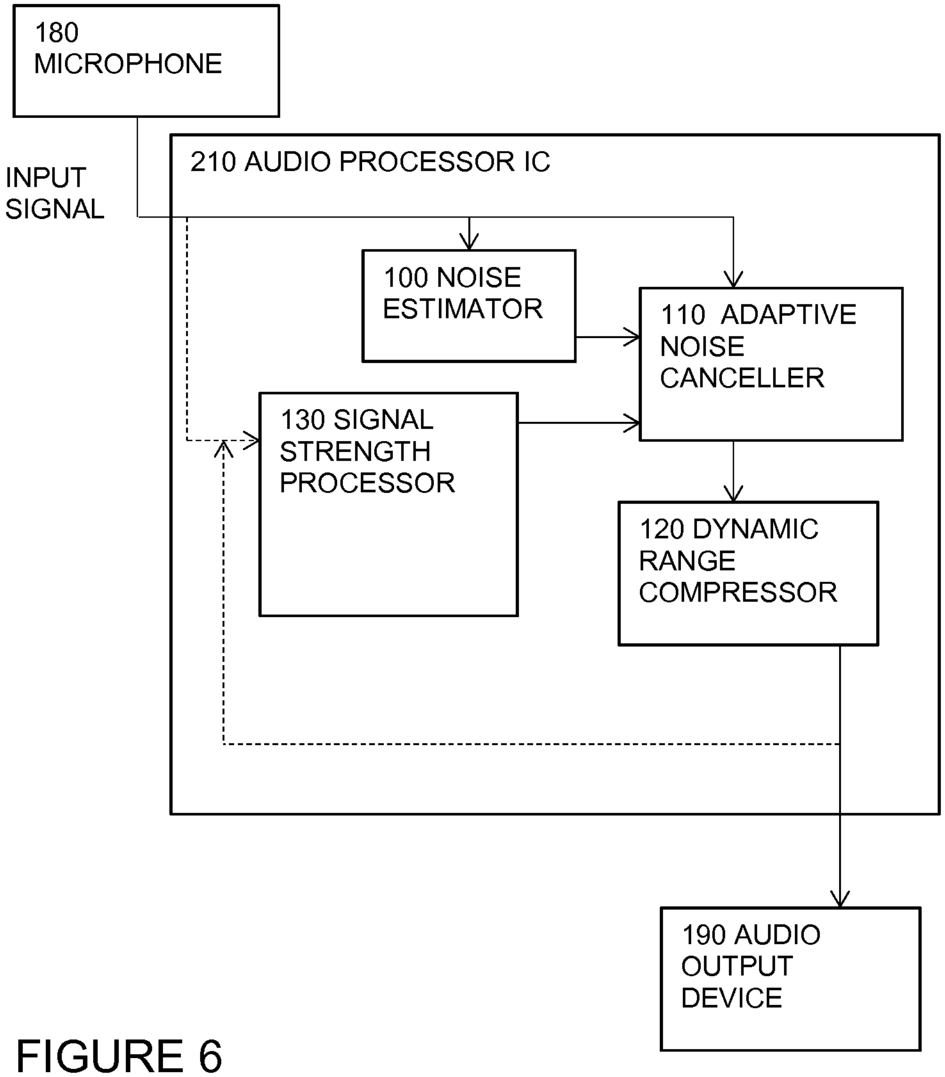
FIG. 6 shows a schematic view of a hearing device having an audio processor according to an embodiment.

FIG. 6, Hearing Device

FIG. 6 shows a schematic view of a system such as a hearing aid, hearing assist or hearing protection device or voice transmission system or mobile phone network, having an audio processor according to an embodiment showing a typical application. Again this shows an embodiment similar to that of FIG. 1, and corresponding parts are shown with the same reference signs. In this case the audio processor is in the form of an integrated circuit IC 210, and the input signal is provided by a microphone 180. The processed output is fed to an audio output device 190 such as a speaker or earphone or a recording device, or similar. There may be other processing stages or data storage for time shifting, or transmission paths such as mobile network or voice over IP (Internet Protocol) (VoIP) for example, between the microphone and the audio processor and between the audio processor and the audio output device.

FIG. 7 DRC Before ANC

FIG. 7 shows a schematic view of an audio processor according to an embodiment in which the DRC operates ahead of the ANC (Adaptive Noise Canceller). Other arrangements combining the DRC and the ANC are possible. The ANC being dependent on signal strength as described above will still work, though the usual practice is to have the ANC first so as to clean up the input signal close to the source such as the microphone, before other processing such as the DRC is carried out.

Figure 8:
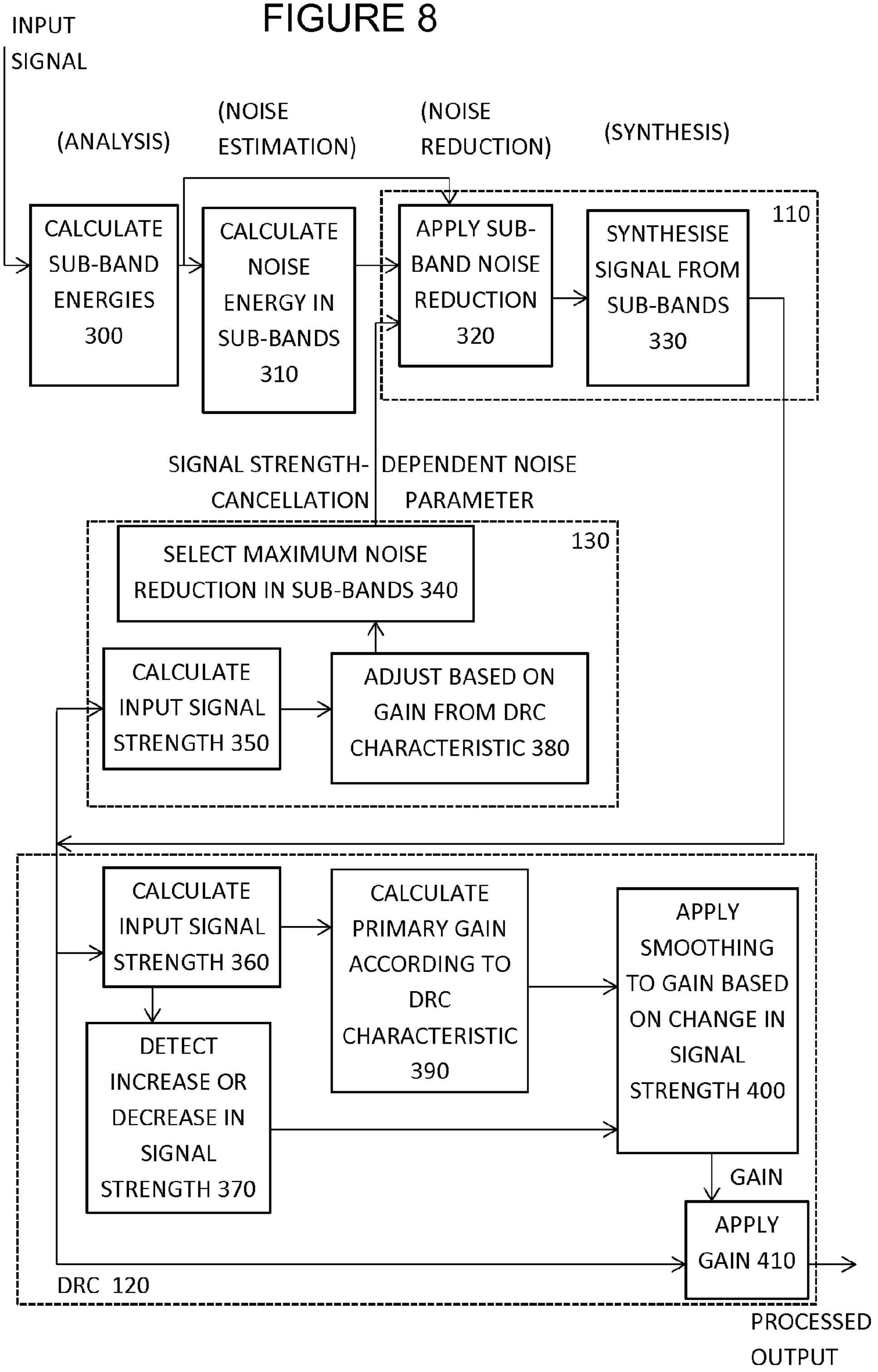
FIG. 8 shows a schematic view of an audio processor according to an embodiment having a noise cancellation parameter based on an input signal after noise cancellation.
Figure 9:
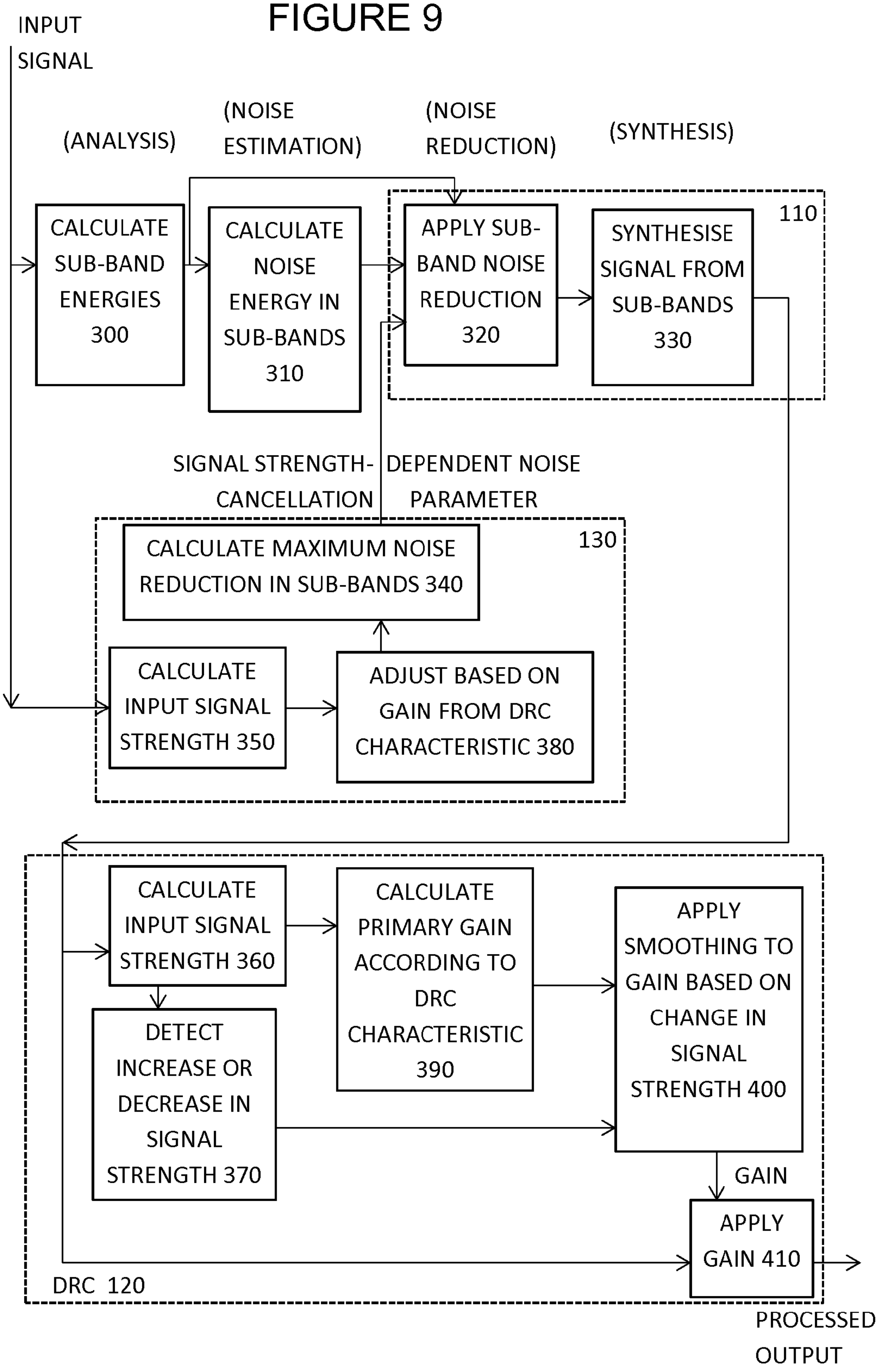
FIG. 9 shows schematic view of an audio processor according to an embodiment having a noise cancellation parameter based on an input signal before noise cancellation.

FIGS. 8 and 9, Embodiments with Different Inputs for Signal Strength Estimation for the Noise Cancellation Parameter FIGS. 8 and 9 illustrate two examples of modules and connections, to illustrate possible implementations for various of the modules described above in FIGS. 1 to 7 and to illustrate different alternatives for the input for signal strength estimation for the noise cancellation parameter. In the first scenario, shown in FIG. 8, the output of the ANC is fed as the input of the signal strength processor 130 for determining the parameter to be passed to the ANC. In the second scenario (FIG. 9) the original input signal before processing by the ANC is fed to the input to the signal strength processor. The computation requirement of FIG. 8 will tend to be lower than that for FIG. 9, however, the FIG. 9 arrangement is likely to be more accurate.

In the examples of FIGS. 8 and 9, the ANC 110 has two main modules, one for applying sub-band noise reduction 320 and one for synthesising the signal from the sub-bands 330. Module 320 for applying the sub-band noise reduction is coupled to receive results of calculating noise energy in each sub-band, from a module 310. Module 320 and module 310 also receive the output of module 300 for calculating the sub-band energies in the input signal.

There is also a signal strength processor 130 having three modules as follows. There is one module 340 for selecting a maximum noise reduction in each sub-band, for output to the ANC as the noise cancellation parameter, one module 350 for calculating an input signal strength based on the output of the ANC, and a module 380 for adjusting the signal strength estimate based on a gain derived from the DRC characteristic.

The DRC 120 is shown as having five modules as follows. There is a module 360 for calculating input signal strength, fed from the output of the ANC, and providing an output to a module 390 for calculating a primary gain according to a DRC characteristic of gain versus signal strength. This module feeds a gain output to a module 400 for applying a smoothing to changes in the gain, based on an input from module 370 for detecting a change in signal strength. This detector detects whether there is an increase or a decrease in the signal strength. The smoothed gain output is then fed to module 410 for applying the gain to the input signal, in this case the input signal after the ANC processing. Each module involved in the ANC and DRC and basic interactions between them are briefly explained below. Other implementations and arrangements of modules are feasible, there are many possible alternatives.

Analysis, by Module 300

This module calculates the sub-band energy of the input signal. It can be implemented in various ways, one example uses a Fast Fourier Transform (FFT) method on an overlapping window of a specified frame size to the input signal. The frames may have different size of overlapping windows.

Noise Estimator Module 310

This module can be implemented in various ways using established methods as discussed above, to estimate the energy of noise in all the sub-bands. It is coupled to use the output of analysis method and can use a statistical model for estimating the noise power in each sub-band.

Adaptive Noise Canceller (ANC) Module

There are various known ways of performing noise estimation and subsequent noise cancellation on an audio signal. Two known approaches to noise estimation are described in the articles: "Noise power spectral density estimation based on optimal smoothing and minimum statistics," R. Martin, IEEE Trans. on Speech Audio Processing, vol. 9, no. 5, pp. 504-512, Jul. 2001; and "A noise-estimation algorithm for highly non-stationary environments," S. Rangachari et al., Speech Communication, vol. 48, no. 2, pp. 220-231, 2006. Two known techniques for reducing noise are Wiener filtering and spectral subtraction. Spectral subtraction is described in the article "Suppression of Acoustic Noise in Speech Using Spectral Subtraction", S. F. Boll, IEEE Trans. on Acoustics, Speech, and Signal Processing, Vol. ASSP-27, No. 2, Apr. 1979, pp. 113-120. The conventional sub-band subtraction technique in classical noise reduction algorithms starts by estimating the noise in each sub-band and subsequently subtracts a predefined amount in each band (bin) to reduce the noise present. This approach is often referred to as a "blind" noise reduction technique since there is no prior knowledge about the noise type or the nature of the noise present.

Unfortunately, there are many noise types which differ in their form. In addition to stationary and non-stationary types of noise there are many other types of narrowband as well as broadband noises which can impair the quality of an audio signal. This presents conflicting problems for fixing the attenuation parameters for a blind noise canceller. If the parameter settings are set too aggressively, then the presence of some noise types is likely to adversely affect the speech quality, resulting in a metallic speech or “piping” effect. On the other hand, if the attenuation parameters are set too modestly, then it is likely that the amount of noise suppression for many noise types will not be sufficient to make a significant subjective difference in improving the voice quality when noise is present with the speech. Note: in the case of specific noise types which may be characterised or pre-determined, the noise canceller can be “tuned” to suppress this particular type of noise which may be present at a particular frequency, multiple frequencies or frequency band(s).

Noise Reduction 320

This module carries out the noise reduction on the input signal and can be implemented in various ways. In one example, where there are bands or sub-bands, it calculates the weights according to the estimated noise power in each sub-band. The sub-band energy is multiplied by the computed weight according to the noise cancellation parameter fed from the signal strength processor 130. In this example the parameter is in the form of the selected Maximum Noise Reduction, fed from module 340, as described below.

Synthesis 330

This module rebuilds the signal by combining the outputs of the noise reduction module. This can be implemented for example using the overlap-add method using the weighted sub-bands produced by the Noise Reduction module 320.

Input Signal Strength Calculator 360

This module calculates the signal strength of the input signal to the DRC. This result is fed to two further modules, one for calculating primary gain 390, and the other for detecting an increase or a decrease in signal strength 370.

Detector for Detecting Increase or Decrease 370

This module monitors the calculated signal strength for changes, so as to indicate whether there is an increase or decrease over a given period. This can be regarded as determining whether currently there is an attack or release mode of operation. The attack mode occurs when the signal strength increases with incoming burst of signal; conversely, release mode occurs at the end of the burst of signal as the signal strength over the period decreases. This indication is used by the smoother module 400 for applying smoothing to the gain Calculate Primary Gain (According to Compressor Curve) 390

This module computes the primary compression gain according to the smoothed signal power and according to the DRC compressor curve characteristic. The compressor curve is a characteristic of gain versus signal strength designed to compress (reduce the gain of) high power (higher signal strength, corresponding to louder) parts of the input signal relative to lower power (lower signal strength corresponding to quieter) parts. This may involve expanding (increasing the gain of) the lower power parts of the incoming signal. A DRC often encompasses an expansion region for low power input; a unity gain region for mid-range input signals; and a compression region for high power input signals.

Gain Smoothing 400

This module can be implemented in various ways and uses the primary gain calculated by the Compressor Curve as input. The gain is further smoothed in accordance to the detection of either increasing signal strength (attack mode) or decreasing (release mode) provided from module 370. Then the smoothed gain can be applied to the input signal by the apply gain part 410, typically implemented as a multiplier or attenuator. Adjusting smoothing factors and/or attack/release times can help reduce the noticeable ‘waving’ effect of noise level during the gaps in the speech. By making the smoothing dependent on whether the signal is in attack or release mode, this can enable the gain to adapt differently when needed. Additionally, relatively short attack time for example can rapidly reduce the gain for sharp increases in signal strength, while release time can be made relatively longer so that, for example, dips between signal peaks are not followed too quickly, hence reducing noticeable oscillations in the amounts of noise cancellation.

Adjust Based on Gain, 380

This module of the signal strength processor can be used to adjust the raw signal strength values obtained by the input signal strength calculation module 350, to apply some gain compression, so as to match more closely the signal strength perceived by a user. This can be achieved by applying a gain taken from the DRC characteristic of gain versus signal strength. If there is any further processing after the DRC, then this module can be adapted further to make corresponding adjustment to the raw signal strength values. The adjusted signal strength is fed to the next module 340, for generating the signal strength dependent noise cancellation parameter, in the form of a selection of maximum noise reduction.

Maximum Noise Reduction Selector 340

This module selects the Maximum Noise Reduction for each sub-band for output as the noise cancellation parameter for use by the ANC. It can be implemented in various ways. This parameter is used in the ANC module in order to limit the sub-band reduction weights. For very weak or no input signals the selection of maximum noise reduction is based on a point at lower parts of the DRC curve leading to a parameter indicating expansion or less dynamic range compression of the overall input signal and noise. In this case the inherent hardware noise is prominent and therefore more aggressive noise reduction is required to adequately attenuate the circuit noise. Therefore the selection of Maximum Noise Reduction increases to, for example, 95% attenuation in the sub-bands. The actual noise reduction in each band still depends on the amount of noise detected in each band. As the input signal level increases, the selection of Maximum Noise Reduction is based on the upper part of the DRC curve resulting in more dynamic range compression of the overall input signal and noise. In this case the inherent hardware noise is compressed (attenuated) by the DRC and with the noise no longer prominent, less noise reduction is required by the ANC module to remove any residual circuit noise. Therefore, the selected Maximum Noise Reduction reduces to, for example, 10% attenuation in the sub-bands, which leaves 90% of the input (or ambient) noise intact. Other percentages can be used as desired. The Maximum Noise Reduction is therefore dependent on the signal strength of the input signal (which can encompass the magnitude, voltage level, or power for example) and can be adjusted continuously or in steps of for example 5% or 10% attenuation. The step size should make the granularity sufficiently fine that a listener does not perceive step changes in noise level as the signal level changes. This may depend on the DRC curve or other factors. The range of changes can be between the specified maximum and minimum limits of, for example, 95% and 10% in this implementation. In a typical example the noise cancellation parameter is updated at the same rate as the ANC is updated, for example every 20 ms, though other update frequency can be used and in some cases it can be varied to save power when the input signal shows little change for example.

This approach of making the ANC dependent on signal strength can help avoid the disadvantage of the ANC module running aggressively at all times which can adversely affect the quality of pure speech with no ambient noise present. By selecting the maximum noise reduction based on signal strength, the embodiments as described can reduce or avoid distorting the input signal, for example improving incoming voice quality or speech intelligibility. Additionally, the embodiments provide reduced cancellation when there is higher signal strength such that more of the desirable ambient type noise, present when the signal strength is higher, can be retained, while providing more cancellation of undesirable circuit type noise when there is low signal strength.

FIG. 9, Input to Signal Strength Processor Before ANC

FIG. 9 shows a schematic view similar to that of FIG. 8 but with one notable difference as follows. While in FIG. 8 the output of the ANC is fed as an input to module 360 for calculating input signal strength for the signal strength processor 130, in FIG. 9 this input is the input signal before processing by the ANC. The signal strength required for determining the primary gain of the DRC is still calculated based on the signal output from the ANC. This arrangement of FIG. 9 can improve the accuracy of the calculation, though the arrangement in FIG. 8 can reduce the amount of computation needed, and thus save some processing resource and battery power. This is partly because the same calculation is carried out by modules 350 and 360, so the processing can be shared.

Figure 10:
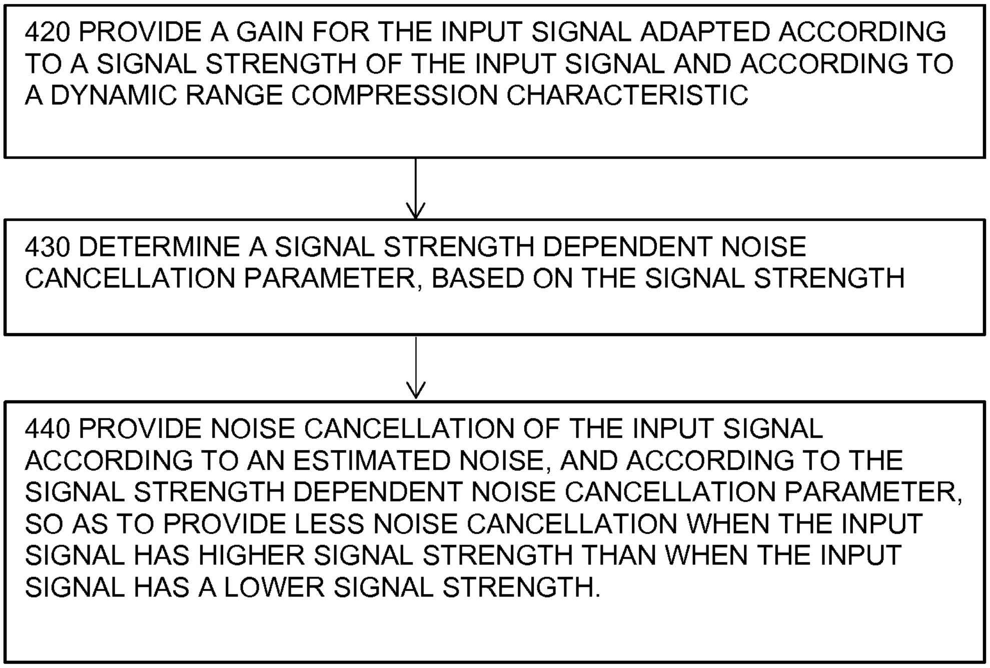
FIG. 10 shows steps in a method of processing an input signal according to an embodiment.

FIG. 10, Method Steps

FIG. 10 shows method steps according to an embodiment. There is a step of providing a gain (420) for the input signal adapted according to a signal strength of the input signal and according to a dynamic range compression characteristic. There is a step of determining a signal strength dependent noise cancellation parameter (430), based on the signal strength and providing noise cancellation of the input signal (440) according to an estimated noise, and according to the signal strength dependent noise cancellation parameter. This is so as to provide less noise cancellation when the input signal has higher signal strength than when the input signal has lower signal strength. Other embodiments can have additional steps, for example using any of the features described above.

Figure 11:
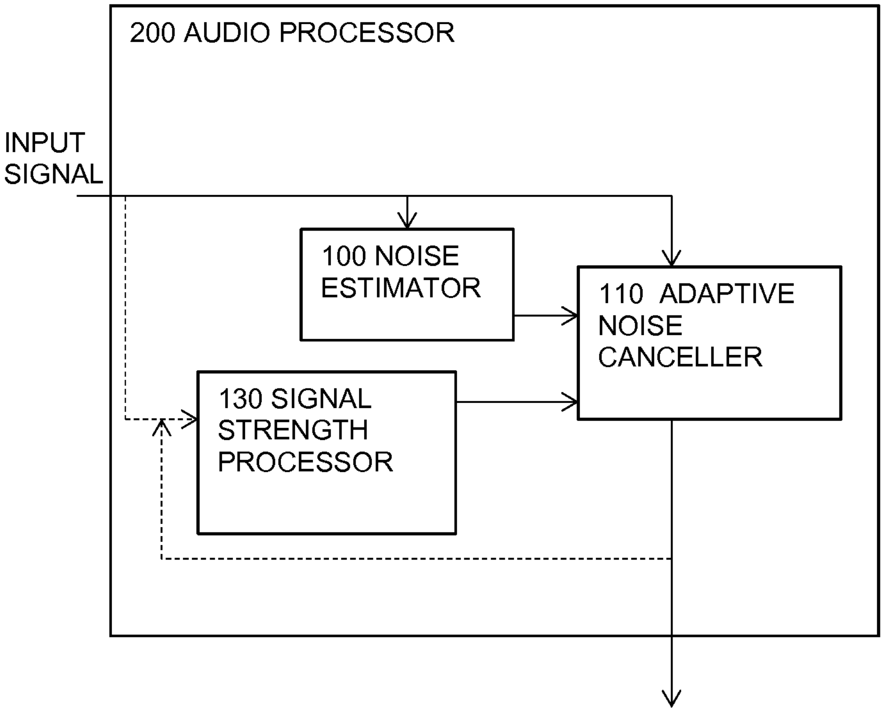
FIG. 11 shows a schematic view of an audio processor according to an embodiment without a DRC.

FIG. 11, Example without DRC

FIG. 11 shows an example similar to FIG. 1, and corresponding reference signs have been used, but without the DRC. This is to show that the signal strength dependency of the ANC can be applied where the system does not incorporate a DRC. There is still a signal strength processor to link the amount of noise attenuation to the signal strength of the input signal. This is to say that, as the input signal increases the noise attenuation of the ANC module decreases. Conversely, if there're little or no signal present, then the noise attenuation of the ANC module increases to remove the inherent circuit noise. In this scenario, as there is no DRC, therefore it is not expected that the circuit noise is compressed as the input signal increases; however it can be assumed that the subjective effect of the inherent circuit noise will be gradually 'masked' by the increase in the level of input signal. Therefore there is still some benefit in making the ANC operation dependent on signal strength. The other important benefit of providing reduced cancellation when there is higher signal strength is that more of the desirable ambient type noise, present when the signal strength is higher, can be retained, while providing more cancellation of undesirable circuit type noise when there is low signal strength.

Other embodiments and variations can be envisaged within the scope of the claims.

The invention claimed is:

1. An audio processor suitable for processing an input signal, comprising:

a noise estimator for receiving the input signal and outputting an estimated noise of the input signal;

a signal strength processor for receiving an indication of the signal strength of the input signal in terms of the strength of the combination of any noise components and audio information content of the signal and configured to determine a signal strength dependent noise cancellation parameter based on the indication of the signal strength of the input signal;

an adaptive noise canceller operatively coupled to the noise estimator and the signal strength processor and configured to provide noise cancellation of the input signal according to an estimated noise from the noise estimator and configured to provide reduced noise cancellation according to the signal strength dependent noise cancellation parameter to provide less noise cancellation to retain more of the noise in the input signal when the input signal has higher signal strength in terms of strength of the combination of any noise components and audio information content of the input signal than when the input signal has lower signal strength; and a dynamic range compressor configured to provide a gain for the input signal adapted according to a signal strength of the input signal, in terms of strength of a combination of any noise components and audio information content of the input signal.

2. The audio processor of claim 1, wherein the signal strength processor comprises a selector configured to select a maximum amount of noise cancellation by the adaptive noise canceller according to the signal strength, and wherein the signal strength dependent noise cancellation parameter comprises an indication of this selection.

3. The audio processor of claim 1, wherein the adaptive noise canceller is configured to provide variations in the noise cancellation according to a variation in the signal strength dependent noise cancellation parameter, with a granularity sufficiently fine that a listener does not perceive step changes in a noise level.

4. The audio processor claim 1, wherein the signal strength processor comprises:

a signal strength estimator configured to determine a signal strength of the input signal; and an adjuster configured to generate a gain adjusted signal strength indication according to a characteristic of gain versus signal strength used by the dynamic range compressor and to determine the signal strength dependent noise cancellation parameter according to the gain adjusted signal strength indication.

5. The audio processor of claim 1 and the signal strength processor being coupled to determine the signal strength dependent noise cancellation parameter according to the input signal before the adaptive noise cancellation.

6. The audio processor of claim 1 and the signal strength processor being coupled to determine the signal strength dependent noise cancellation parameter according to the input signal after the adaptive noise cancellation.

7. The audio processor of claim 1, further comprising a change detector configured to detect an increase or a decrease in the signal strength of the input signal;

wherein the dynamic range compressor comprises a smoother configured to smooth changes in the gain according to the detected changes in the input.

8. The audio processor of claim 1, further comprising a frequency band analyser configured to determine powers of the input signal in a plurality of frequency bands;

wherein the adaptive noise canceller comprises canceller components each configured to operate on a respective one of the plurality of frequency bands.

9. An integrated circuit comprising the audio processor of claim 1.

10. A hearing device comprising:

an audio processor according to claim 1; a microphone coupled thereto to provide an input signal to the audio processor; and an audio output device coupled to the audio processor.

11. A method of processing an input signal, comprising:

providing a gain for the input signal adapted according to a signal strength of the input signal, in terms of strength of a combination of any noise components and audio information content of the input signal, and according to a dynamic range compression characteristic;

determining a signal strength dependent noise cancellation parameter based on the signal strength; and providing noise cancellation of the input signal according to an estimated noise and providing reduced noise cancellation according to the signal strength dependent noise cancellation parameter to provide less noise cancellation to retain more of the noise in the input signal when the input signal has higher signal strength in terms of strength of the combination of any noise components and audio information content of the input signal than when the input signal has lower signal strength.

12. The method of claim 11, wherein the determining the signal strength dependent noise cancellation parameter comprises selecting a maximum amount of noise cancellation by the adaptive noise canceller according to the signal strength.

13. The method of claim 11, wherein the noise cancelling comprises making variations in the noise cancellation according to a variation in the signal strength dependent noise cancellation parameter, with a granularity sufficiently fine that a listener does not perceive step changes in a noise level.

14. The method of claim 11, wherein the determining the signal strength dependent noise cancellation parameter comprises:

determining a signal strength of the input signal;

generating a gain adjusted signal strength indication according to the dynamic range compression characteristic; and determining the signal strength dependent noise cancellation parameter according to the gain adjusted signal strength indication.

15. The method of claim 11, wherein the determining the signal strength dependent noise cancellation parameter is made using the input signal before the noise cancellation is applied.

16. The method of claim 11 further comprising:

detecting an increase or a decrease in the signal strength of the input signal; and smoothing changes in the gain according to the detected change in the input.

17. A non-transitory computer readable medium that stores computer executable instructions for performing steps, comprising:

providing a gain for an input signal adapted according to a signal strength of the input signal, in terms of strength of a combination of any noise components and audio information content of the input signal, and according to a dynamic range compression characteristic;

determining a signal strength dependent noise cancellation parameter based on the signal strength; and providing noise cancellation of the input signal according to an estimated noise and providing reduced noise cancellation according to the signal strength dependent noise cancellation parameter to provide less noise cancellation to retain more of the noise in the input signal when the input signal has higher signal strength in terms of strength of the combination of any noise components and audio information content of the input signal than when the input signal has lower signal strength.

18. The non-transitory computer readable medium of claim 17, wherein the determining the signal strength dependent noise cancellation parameter comprises selecting a maximum amount of noise cancellation by the adaptive noise canceller according to the signal strength.

19. The non-transitory computer readable medium of claim 17, wherein providing the noise cancellation comprises making variations in the noise cancellation according to a variation in the signal strength dependent noise cancellation parameter, with a granularity sufficiently fine that a listener does not perceive step changes in a noise level.

20. An audio processor suitable for processing an input signal, comprising:

a noise estimator for receiving the input signal and outputting an estimated noise of the input signal;

a signal strength processor for receiving an indication of the signal strength of the input signal in terms of the strength of the combination of any noise components and audio information content of the signal and configured to determine a signal strength dependent noise cancellation parameter based on the indication of the signal strength of the input signal; and an adaptive noise canceller operatively coupled to the noise estimator and the signal strength processor and is configured to provide noise cancellation of the input signal according to an estimated noise from the noise estimator and configured to provide reduced noise cancellation according to the signal strength dependent noise cancellation parameter to provide less noise cancellation to retain more of the noise in the input signal when the input signal has higher signal strength in terms of strength of any combination of any noise components and audio information content of the input signal, than when the input signal has lower signal strength.

* * * * *